(12) United States Patent
Hanebuchi (10) Patent No.: US 7,370,968 B2
(45) Date of Patent: May 13, 2008

(54) OCULAR DEPTH DIMENSION MEASUREMENT APPARATUS (75) Inventor: Masaaki Hanebuchi, Nukata-gun (JP)

(73) Assignee: Nidek Co., Ltd., Gamagori-shi (JP)

( * ) Notice: Subject to any disclaimer, the term of this patent is extended or adjusted under 35 U.S.C. 154(b) by 0 days.

(21) Appl. No.: 11/806,044

(22) Filed: May 29, 2007

(65) Prior Publication Data

US 2007/0279592 A1 Dec. 6, 2007

(30) Foreign Application Priority Data

May 29, 2006 (JP) ............................. 2006-148419

(51) Int. Cl.
*A61B 3/10* (2006.01)
(52) U.S. Cl. ............... 351/211; 351/221; 351/205
(58) Field of Classification Search ............... 351/200, 351/204–206, 208, 211, 220, 221
See application file for complete search history.

(56) References Cited

U.S. PATENT DOCUMENTS

| 5,387,951 | A | * | 2/1995 | Hatanaka | .......... 351/205 |
| 6,779,891 | B1 | | 8/2004 | Barth et al. | |
| 6,806,963 | B1 | | 10/2004 | Wälti et al. | |
| 2007/0002277 | A1 | | 1/2007 | Hanebuchi | |

FOREIGN PATENT DOCUMENTS

| EP | 1 602 320 A1 | 12/2005 |
| JP | A 2-297332 | 12/1990 |
| JP | A 4-272742 | 9/1992 |
| JP | A 5-115437 | 5/1993 |
| JP | A 7-255674 | 10/1995 |
| JP | A 2002-531205 | 9/2002 |
| JP | A 2006-52954 | 2/2006 |

* cited by examiner

*Primary Examiner*—Huy Mai
*Assistant Examiner*—Jack Dinh
(74) *Attorney, Agent, or Firm*—Oliff & Berridge, PLC (57) ABSTRACT

An ocular depth dimension measurement apparatus capable of accurately obtaining an ocular depth dimension. The apparatus has a measurement light projecting optical system with a light source which is arranged to make a part of the light from the light source into first and second measurement light and collect the respective measurement light on first and second measurement surfaces of the eye, an interference optical system with a separation unit arranged to make the light into reference light and an optical path length changing unit which is arranged to synthesize the first and second measurement light respectively with the reference light to make them interfere with each other so as to photo-receive and obtain interference signals of the respective interference light, and a calculation part arranged to calculate the ocular depth dimension based on the interference signals and a driving result of the changing unit.

7 Claims, 5 Drawing Sheets

OCULAR DEPTH DIMENSION MEASUREMENT APPARATUS

BACKGROUND OF THE INVENTION

1. Field of the Invention

The present invention relates to an ocular depth dimension measurement apparatus which performs non-contact measurement of an ocular depth dimension.

2. Description of Related Art

As an apparatus for obtaining an ocular depth dimension, for example, there is known an apparatus which optically performs non-contact measurement of an axial length of an eye. As the apparatus, there is known an apparatus including an projection optical system arranged to project low coherent light onto an eye, an interference optical system arranged to obtain (detect) an interference signal by synthesizing and making the light reflected from a fundus and the light reflected from a cornea interfere with each other, and an optical path length changing member, which obtains the axial length based on the obtained interference signal and the position of the optical path length changing member (see Japanese Patent Application Unexamined Publication Hei02-297332).

However, the above-described apparatus has a problem that the obtained interference signal has a low S/N ratio since the light reflected from the cornea having a high reflectance and the light reflected from the fundus having a low reflectance are made to interfere with each other, so that measurement error is increased. In order to increase the S/N ratio of the interference signal, it is necessary to project strong light onto the eye, which becomes a burden on the eye.

SUMMARY OF THE INVENTION

An object of the invention is to overcome the problems described above and to provide an ocular depth dimension measurement apparatus capable of accurately obtaining an ocular depth dimension.

To achieve the objects and in accordance with the purpose of the present invention, an ocular depth dimension measurement apparatus which performs non-contact measurement of an ocular depth dimension of an examinee's eye has a measurement light projecting optical system including a light source emitting low coherent light, and arranged to make a part of the light from the light source into first measurement light and a part of the light from the light source into second measurement light, and to collect the first measurement light on a first measurement surface of the eye and the second measurement light on a second measurement surface of the eye, an interference optical system including a separation unit arranged to separate a part of the light from the light source to make it into reference light, and an optical path length changing unit arranged to change optical path length of the reference light, arranged, while changing the optical path length of the reference light, and to synthesize the first measurement light reflected by the first measurement surface and the reference light and to make them interfere with each other so as to photo-receive, to synthesize the second measurement light reflected by the second measurement surface and the reference light and to make them interfere with each other so as to photo-receive, and arranged to obtain interference signals of the respective interference light, and a calculation part arranged to calculate the ocular depth dimension of the eye based on the obtained interference signals and a driving result of the optical path length changing unit.

Additional objects and advantages of the invention are set forth in the description which follows, are obvious from the description, or may be learned by practicing the invention. The objects and advantages of the invention may be realized and attained by the apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1A:
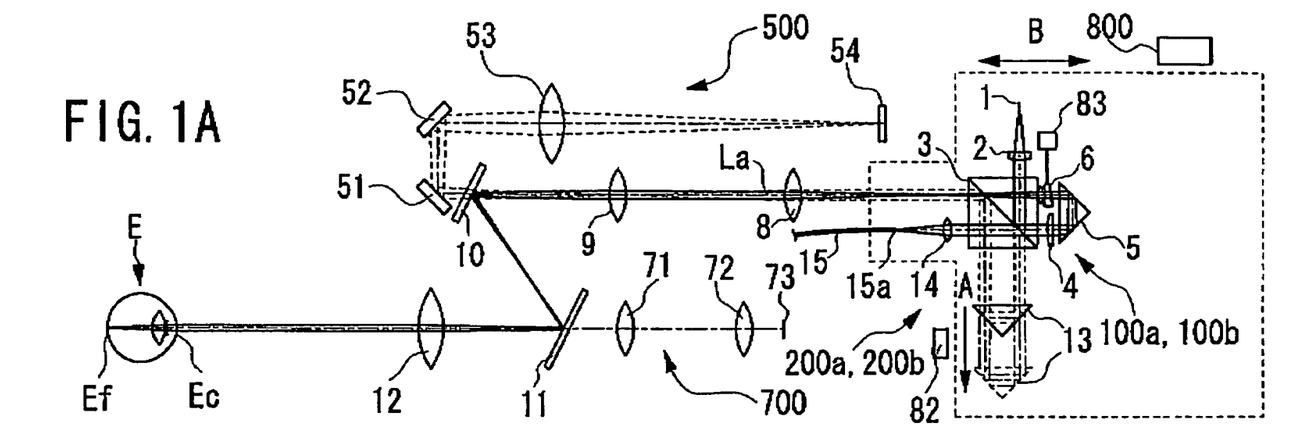
FIGS. 1A and 1B are views showing a schematic configuration of an optical system of an ocular depth dimension measurement apparatus according to one preferred embodiment of the present invention.
Figure 1B:
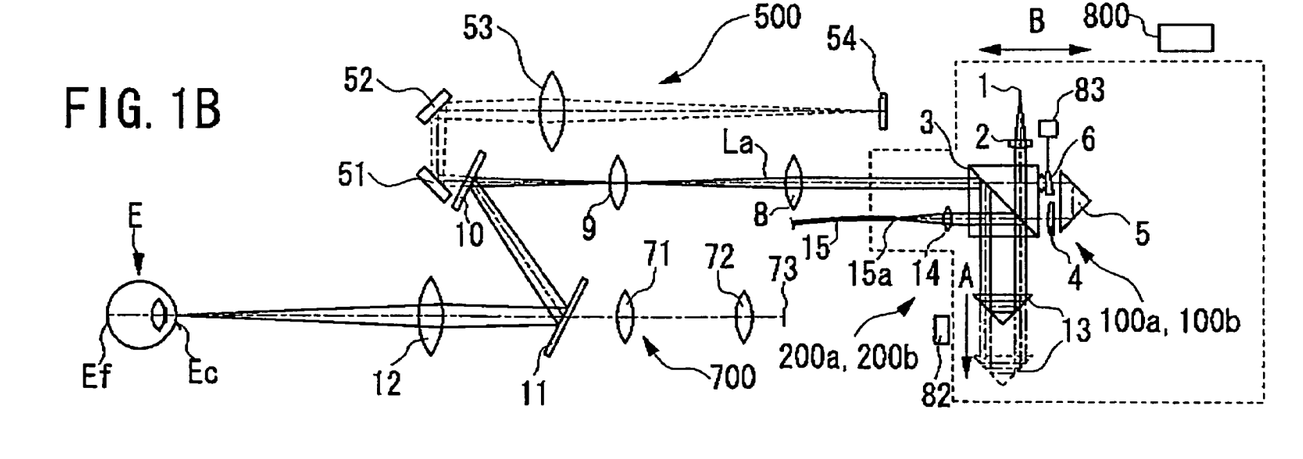

A detailed description of one preferred embodiment of an ocular depth dimension measurement apparatus embodied by the present invention is provided below with reference to the accompanying drawings. FIGS. 1A and 1B are views showing a schematic configuration of an optical system of an ocular depth dimension measurement apparatus according to one preferred embodiment of the present invention. The ocular depth dimension measurement apparatus includes a fundus measurement light projecting optical system 100a, a corneal measurement light projecting optical system 200a, a fundus measurement light photo-receiving optical system 100b, a corneal measurement light photo-receiving optical system 200b, a reference light optical system 500, a spectral optical system 600 (see FIG. 2), and an observation optical system 700. Incidentally, though the ocular depth dimension measurement apparatus of the preferred embodiment includes an alignment optical system arranged to perform alignment of the apparatus in order to have a predetermined positional relationship with an examinee's eye E (the alignment optical system includes an alignment optical system in a working distance direction), a description thereof is omitted since it is essential only that an optical system similar to a known alignment optical system used in an objective eye refractive power apparatus and the like is used.

The projecting optical systems 100a and 200a constitute a measurement light projecting optical system arranged to project measurement light onto the eye E, which includes a light source 1 emitting low coherent light, and makes a part of the light from the light source 1 into corneal measurement light that is defined as first measurement light and a part of the light from the light source 1 into fundus measurement light that is defined as second measurement light, collects the corneal measurement light on a cornea Ec of the eye E that is defined as a first measurement surface and collects the fundus measurement light on a fundus Ef of the eye E that is defined as a second measurement surface.

the photo-receiving optical systems 100b and 200b, the reference light optical system 500 and the spectral optical system 600 constitute an interference optical system arranged to obtain (detect) interference signals by making the measurement light (the corneal measurement light and the fundus measurement light) and reference light interfere with each other, which includes a separation unit (a half mirror 10 in the preferred embodiment) which separates a part of the light from the light source 1 to make it into the reference light, and an optical path length changing unit (a triangular prism 13 and a driving part 82 in the preferred embodiment) which changes optical path length of the reference light, and is arranged, while changing the optical path length of the reference light, to synthesize the corneal measurement light reflected by the cornea Ec and the reference light and make them interfere with each other so as to photo-receive, and to synthesize the fundus measurement light reflected by the fundus Ef and the reference light and make them interfere with each other so as to photo-receive.

The projecting optical system 100a arranged to project the fundus measurement light onto the fundus Ef includes the light source 1, a collimator lens 2, a half mirror 3, a condenser lens 4, a triangular prism 5, a rotary prism 6, a relay lens 8, a relay lens 9, the half mirror 10, a dichroic mirror 11, and an objective lens 12. The light source 1 emits the low coherent light such as an infrared SLD (Super Luminescent Diode). The dichroic mirror 11 reflects the light from the light source 1 and transmits light from an unillustrated light source for anterior-segment illumination.

The prism 6 is rotated around an optical axis La by a driving part 83. The prism 6 is placed at a position deviated from a position conjugate with the fundus Ef (in the preferred embodiment, the position is also deviated from a position conjugate with a pupil), and decenters transmitted light with respect to the optical axis La. Accordingly, the position on the fundus Ef on which the fundus measurement light is collected (projected) is moved in a direction perpendicular to the optical axis La. Besides, a parallel plane plate may be placed at a slant on the optical axis La and be rotated instead of the prism 6.

As shown in FIG. 1A, the light from the light source 1 is made into a parallel light bundle by the lens 2, and after that, a part of the parallel light bundle is reflected by the half mirror 3, is collected on the lens 4, turns back at the prism 5, and is transmitted through the prism 6, then a part of which is transmitted through the half mirror 3, is collected once, and is transmitted through the lenses 8 and 9, then a part of which is reflected by the half mirror 10, is reflected by the dichroic mirror 11, is transmitted through the lens 12, and is collected on the fundus Ef. At this time, an image of the light source 1 is moved (eccentrically rotated) on the fundus Ef by the prism 6 which is rotated around the optical axis La.

The light reflected from the fundus Ef travels on an optical path from the lens 12 to the lens 4 of the projecting optical system 100a in the reverse direction, and a part of the reflected light is transmitted through the half mirror 3, is collected on a condenser lens 14, and enters an end portion 15a of an optical fiber 15. That is to say, the photo-receiving optical system 100b for photo-receiving the fundus measurement light reflected from the fundus Ef includes the lens 12, the dichroic mirror 11, the half mirror 10, the lenses 9 and 8, the half mirror 3, the prisms 6 and 5, the lenses 4 and 14, and the optical fiber 15. At this time, the movement (eccentric rotation) of the light reflected from the fundus Ef (the image of the light source 1) is cancelled by the prism 6.

The projecting optical system 200a arranged to project the corneal measurement light onto the cornea Ec includes the light source 1, the lens 2, the half mirror 3, the triangular prism 13, the lenses 8 and 9, the half mirror 10, the dichroic mirror 11, and the lens 12.

As shown in FIG. 1B, the light from the light source 1 is made into a parallel light bundle by the lens 2, and after that, a part of the parallel light bundle is transmitted through the half mirror 3, turns back at the prism 13, then a part of which is reflected by the half mirror 3, is transmitted through the lens 8, is collected on the lens 9 once, then a part of which is reflected by the half mirror 10, is reflected by the dichroic mirror 11, is transmitted through the lens 12, and is collected on the cornea Ec. The projecting optical system 200a according to the preferred embodiment shares an optical path from the light source 1 to the half mirror 3 and an optical path from the half mirror 3 to the lens 12 with the projecting optical system 100a.

The light reflected from the cornea Ec travels on an optical path from the lens 12 to the prism 13 of the projecting optical system 200a in the reverse direction, and a part of the reflected light is reflected by the half mirror 3, is collected on the lens 14, and enters the end portion 15a. That is to say, the photo-receiving optical system 200b for photo-receiving the corneal measurement light reflected from the cornea Ec includes the lens 12, the dichroic mirror 11, the half mirror 10, the lenses 9 and B, the half mirror 3, the prism 13, the lens 14, and the optical fiber 15.

The reference light optical system 500 arranged to generate the reference light which is synthesized with the fundus measurement light and the corneal measurement light includes the light source 1, the lens 2, the half mirror 3, the prism 13, the lenses 8 and 9, total reflection mirrors 51 and 52, a relay lens 53, and a reference mirror 54. The prism 13 which moves in a direction of an arrow A is driven by the driving part 82 to change the optical path length of the reference light. The prism 13 is placed at a position which is on a common optical path where the corneal measurement light and the reference light pass (i.e., the common optical path is an optical path of the projecting optical system 200a or an optical path of the photo-receiving optical system 200b; which is shared with the reference light optical system 500), and not on an optical path where the fundus measurement light passes (an optical path of the projecting optical system 100a and an optical path of the photo-receiving optical system 100b). With such an optical arrangement, optical path length of the corneal measurement light and the optical path length of the reference light are simultaneously changed with the movement of the prism 13.

The optical arrangement shown in FIGS. 1A and 1B is an example of the above-described optical arrangement, where the reference mirror 54 that is a reference surface is placed so that the optical path length of the corneal measurement light from the light source 1 to the cornea Ec and the optical path length of the reference light from the light source 1 to the reference mirror 54 approximately coincide (to the extent that the interference signal can be obtained). The light from the light source 1 travels on the same optical path as in the projecting optical system 200a, and a part of the light is transmitted through the half mirror 10, is reflected by the mirrors 51 and 52, is transmitted through the lens 53, turns back at the reference mirror 54, is transmitted through the lens 53, is reflected by the mirrors 52 and 51, then a part of which is transmitted through the half mirror 10, is synthesized with the corneal measurement light reflected from the cornea Ec, and is made to interfere with each other. The interference light generated by the corneal measurement light and the reference light travels on the same optical path as in the photo-receiving optical system 200b, and enters the end portion 15a. With this configuration, even if the position of the prism 13 is changed, the entire optical path length of the corneal measurement light (the optical path length from the light source 1 to the cornea Ec and the optical path length from the cornea Ec to the end portion 15a) and the entire optical path length of the reference light (the optical path length from the light source 1 to the reference mirror 54 and the optical path length from the reference mirror 54 to the end portion 15a) are maintained approximately equal to the extent that the corneal measurement light and the reference light can be made to interfere with each other, and thereby the interference light is always generated by the corneal measurement light and the reference light and enters the end portion 15a as long as a working distance of the apparatus with respect to the eye E is appropriate.

In addition, when the optical path length of the reference light is changed by the movement of the prism 13, there is a case where the entire optical path length of the fundus measurement light (the optical path length from the light source 1 to the fundus Ef and the optical path length from the fundus Ef to the end portion 15a) which changes in accordance with an axial length of the eye E, and the entire optical path length of the reference light become approximately equal to the extent that the fundus measurement light and the reference light can be made to interfere with each other. In this case, the reference light having turned back at the reference mirror 54 turns back at the prism 13, is reflected by the half mirror 3, is synthesized with the fundus measurement light reflected from the fundus Ef, and is made to interfere with each other. The interference light generated by the fundus measurement light and the reference light is collected on the lens 14 and enters the end portion 15a.

The light reflected from the fundus Ef, however, has less light intensity than the light reflected from the cornea Ec. Accordingly, in order to compensate for a difference in strength between the interference light by the fundus measurement light and the interference light by the corneal measurement light, for example, it is preferable that an attenuating filter is placed on the optical path where the corneal measurement light passes (e.g., between the half mirror 3 and the prism 13). Alternatively, it is preferable that transmittance/reflectance of the half mirror 3 is adjusted. Alternatively, it is preferable that a polarization beam splitter is placed instead of the half mirror 3 and a λ/4 plate is placed between the half mirror 10 and the reference mirror 54, and a polarization direction of the λ/4 plate is adjusted.

Figure 2:
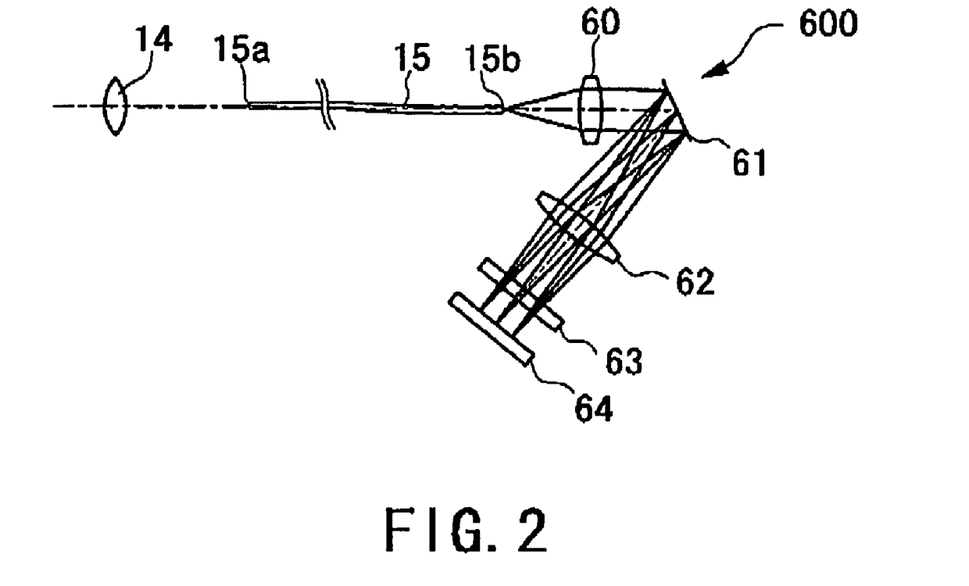
FIG. 2 is a view showing a schematic configuration of a spectral optical system of the ocular depth dimension measurement apparatus.

FIG. 2 is a view showing a schematic configuration of the spectral optical system of the ocular depth dimension measurement apparatus. The spectral optical system (spectrometer part) 600 arranged to disperse the interference light into frequency (wavelength) components includes a collimator lens 60, agrating mirror (diffraction grating) 61 that is defined as a dispersing unit, a condenser lens 62, a cylindrical lens 63, and a photodetector 64. The photodetector 64 is a one-dimensional photodetector (a line sensor) having sensitivity to an infrared range.

The interference light generated by the corneal measurement light and the reference light and the interference light generated by the fundus measurement light and the reference light enter the end portion 15a and exit from an end portion 15b of the optical fiber 15. Then, the respective interference light exiting from the end portion 15b, of which light bundle diameters are enlarged by the lens 60, is dispersed into the frequency components by the grating mirror 61, is transmitted through the lenses 62 and 63, and is collected on a photo-receiving surface of the photodetector 64. Besides, the light bundle diameters of the interference light after transmitted through the lens 60, the spaces between gratings of the grating mirror 61, incident angles of the interference light on the grating mirror 61, the lens 62, and the photodetector 64 are optimized in consideration of a measurement range (e.g., 40 mm) and a resolution of the eye E in a depth direction.

The observation optical system 700 includes the lens 12, the dichroic mirror 11, a relay lens 71, an image-pickup lens 72, and an image-pickup element 73 having sensitivity to the infrared range. The image-pickup element 73 is placed at a position approximately conjugate with the pupil of the eye E. An anterior segment of the eye E is illuminated by an unillustrated infrared light source for anterior-segment illumination, and an image of the anterior segment is picked up by the image-pickup element 73.

Figure 3:
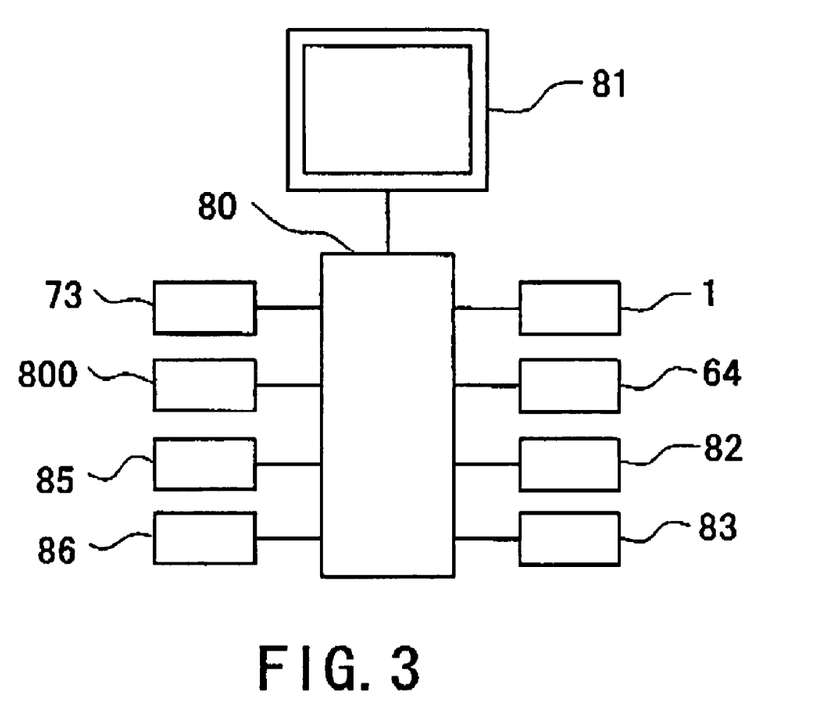
FIG. 3 is a schematic block diagram of a control system of the ocular depth dimension measurement apparatus.

FIG. 3 is a diagram showing a configuration of a control system of the ocular depth dimension measurement apparatus. A calculation and control part 80 which drives and controls the apparatus is connected with the light source 1, the photodetector 64, the image-pickup element 73, a monitor 81, the driving parts 82 and 83, a memory 85, an input part 85, a visibility correcting unit 800 which is described later, and the like. The driving parts 82 and 83 are arranged so that their driving amounts can be detected by a pulse motor or the like, The memory 85 stores a measurement value and the like of an ocular depth dimension, e.g., the axial length obtained by the calculation and control part 80. The input part 86 includes a variety of operation switches such as a measurement start switch and a measurement mode changeover switch.

A detailed description of measurement of the axial length of the eye E performed by using the apparatus having the above-described configuration will be provided.

While an alignment state of the apparatus with respect to the eye E is observed on the monitor 81, the apparatus is moved in an up-and-down direction, a right-and-left direction and a back-and-forth direction by operation of an unillustrated joystick or the like, and is aligned to have a predetermined positional relationship with the eye E. More specifically, the apparatus is moved in the up-and-down direction and the right-and-left direction so that a corneal vertex or a pupil center of the eye E approximately coincides with the optical axis La, and is moved in the back-and-forth direction so that the working distance of the apparatus with respect to the eye E becomes equal to a predetermined appropriate working distance (e.g., 40 mm).

When the measurement start switch is pressed, the calculation and control part 80 controls to emit the low coherent light from the light source 1. The light from the light source 1 is divided into two by the half mirror 3, and one of the light is collected on the cornea Ec via the projecting optical system 200a, and enters the reference mirror 54 via the reference light optical system 500. The other light is collected on the fundus Ef via the projecting optical system 100a, and enters the reference mirror 54 via the reference light optical system 500. The corneal measurement light reflected from the cornea Ec is synthesized with the reference light reflected by the reference mirror 54, is made into the interference light, and is photo-received on the photodetector 64 via the photo-receiving optical system 200b. In addition, the fundus measurement light reflected from the fundus Ef is synthesized with the reference light reflected by the reference mirror 54, is made into the interference light, and is photo-received on the photodetector 64 via the photo-receiving optical system 100b.

Spectral information on interference fringes which is obtained at the photodetector 64 is inputted to the calculation and control part 80 and is analyzed by performing a Fourier transform thereon, whereby eye characteristics of the eye E in the depth direction are obtained.

When calculating the axial length of the eye E, the calculation and control part 80 controls to drive the driving part 82 to move the prism 13, and calculates the axial length of the eye E based on an interference signal, which is obtained based on the spectral information obtained at the photodetector 64, and the optical path length of the reference light which is changed by the movement of the prism 13 (a driving result of the optical path length changing unit).

That is to say, the calculation and control part 80 controls to drive the driving part 82 to move the prism 13 from a reference position indicated in full lines in FIGS. 1A and 1B (e.g., a position such that the optical path of the projecting optical system 200a is made to be shortest) in the arrow A direction so as to gradually change the optical path length of the optical system, through which the corneal measurement light and the reference light pass. For example, the prism 13 is moved in predetermined steps, and the spectral information is obtained more than one time for each of the steps in chronological order, and is stored in the memory 85. In other words, the measurement range of the eye E in the depth direction with the fundus measurement light is changed to the retina side (the rear side) inpredetermined steps (e.g., 2 mm). In the preferred embodiment, a movable amount of the prism 13 is set such that the examinee's eye having the axial length from 14 mm to 40 mm as the measurement range can be measured.

Figure 4:
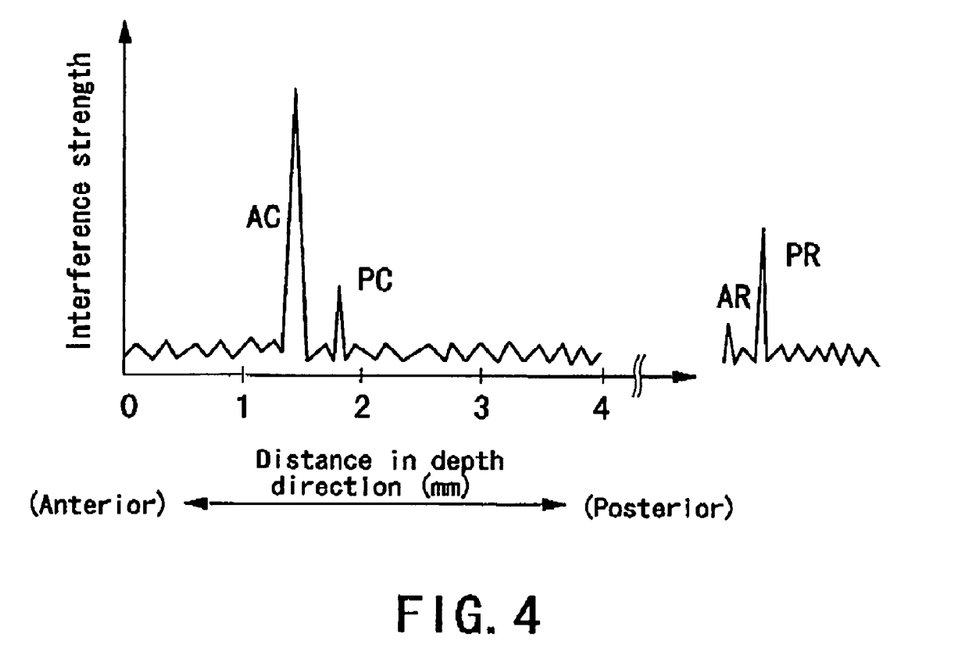
FIG. 4 is a view illustrating an example of strengths of interference signals in a depth direction of an examinee's eye at the time when only the interference signals obtained by making corneal measurement light and reference light interfere with each other are detected.

FIG. 4 is a view for illustrating an example of strengths of the interference signals in the depth direction of the eye E at the time when only the interference signals obtained by making the corneal measurement light and the reference light interfere with each other are detected, which are obtained based on the spectral information obtained when the prism 13 is at the reference position. AC is an interference signal obtained based on light reflected from the anterior surface of the cornea, and PC is an interference signal obtained based on light reflected from the posterior surface of the cornea That is to say, since the interference light generated by the corneal measurement light and the reference light includes the respective light reflected from the corneal anterior and posterior surfaces, the interference signals respectively corresponding thereto are detected.

Meanwhile, the interference signals obtained by making the fundus measurement light and the reference light interfere with each other are in a state of not being detected at this stage. AR is an interference signal obtained based on light reflected from the anterior surface of the retina, and PR is an interference signal obtained based on light reflected from the posterior surface of the retina; however, they are deviated from the measurement range at this stage. This is because since the entire optical path length of the reference light is shorter than the entire optical path length of the fundus measurement light which is changed in accordance with the axial length, the interference light is hardly generated by the fundus measurement light and the reference light.

Figure 5:
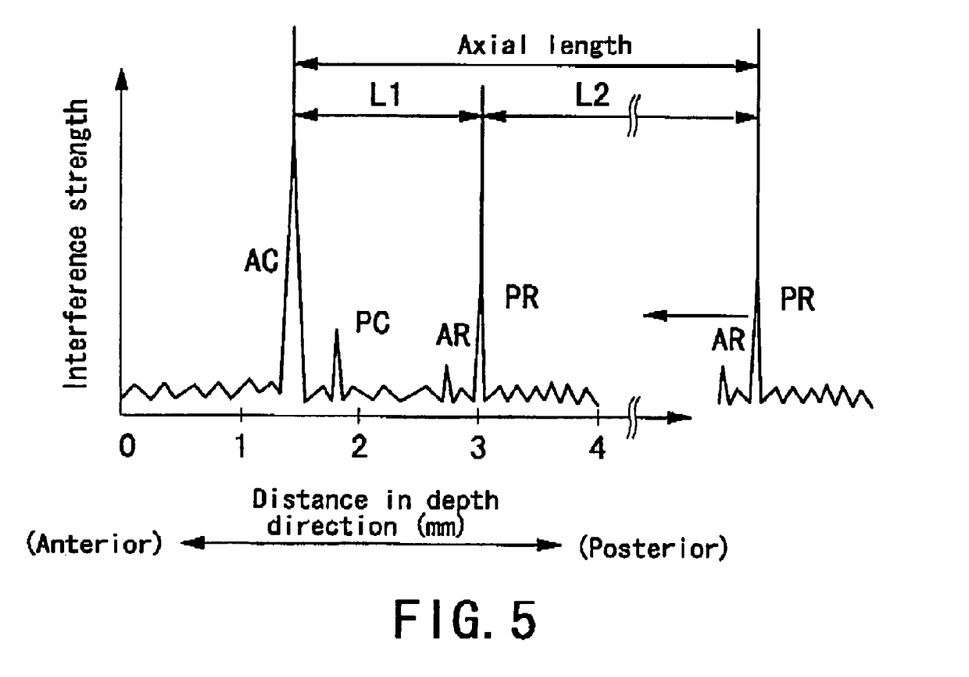
FIG. 5 is a view for illustrating an example of strengths of the interference signals in the depth direction of the eye at the Lime when the interference signals obtained by making the corneal measurement light and the reference light interfere with each other and interference signals obtained by making fundus measurement light and the reference light interfere with each other are detected.

When the optical path length of the reference light becomes longer by the movement of the prism 13 in the arrow A direction and a difference between the optical path length of the fundus measurement light and the optical path length of the reference light becomes smaller, the interference light comes to be generated by the fundus measurement light and the reference light. FIG. 5 is a view for illustrating an example of the strengths of the interference signals in the depth direction of the eye E at the time when the interference signals obtained by making the corneal measurement light and the reference light interfere with each other, and the interference signals obtained by making the fundus measurement light and the reference light interfere with each other are detected. That is to say, since the interference light generated by the fundus measurement light and the reference light includes the respective light reflected from the retinal anterior and posterior surfaces, the interference signals respectively corresponding thereto are detected. If the prism 13 is further moved from the position as in FIG. 5 in the arrow A direction, the interference signals AR and PR come not to be detected in due time.

The position of the prism 13 such that the interference signals AC and PR are detected differs with the axial length. Accordingly, the calculation and control part 80 controls to specify spectral information based on which the interference signals AC and PR are detected, out of the spectral information which is stored in the memory 85 respectively at the movement positions of the prism 13. Then, positional information on the prism 13 (e.g., a movement amount of the prism 13 from the reference position (or, a driving amount of the driving part 82)) at the time when the specified spectral information is obtained. Further, positional information on the interference signals AC and PR in the depth direction is obtained based on the specified spectral information. Incidentally, when the spectral information based on which the interference signals AC and PR are detected is specified, there is a possibility that the interference signals are confused with interference signals corresponding to respective light reflected from the anterior and posterior surfaces of a crystalline lens of the eye E; however, this possibility can be eliminated only if the interference signals which change positions in the depth direction by the movement of the prism 13 are regarded as the interference signals corresponding to the respective light reflected by the retinal anterior and posterior surfaces.

The calculation and control part 80 calculates the axial length based on the positional information on the prism 13 corresponding to the spectral information based on which the interference signals AC and PR are detected, and the positional information on the interference signals AC and PR in the depth direction. In this case, the calculation and control part 80 roughly calculates the axial length based on the positional information on the prism 13, and further calculates the axial length in detail based on the positional information on the interference signals AC and PR.

For example, the calculation and control part 80 calculates a length L1 from the interference signal AC to the interference signal PR in the depth direction based on the spectral information based on which the interference signals AC and PR are detected. Then, the calculation and control part 80 calculates a length L2 in the depth direction based on the movement amount of the prism 13 from the reference position at the time when the spectral information is obtained. Then, by adding the length L2 to the length L1, the axial length is calculated (the axial length=L1+L2).

Incidentally, a calibration is performed on the reference position (the initial position) of the prism 13 by using a model eye having a known axial length, or the like. Then, a corresponding relationship between the length L2 and the position of the prism 13 can be calculated by using the model eye or a predetermined arithmetic expression. Accordingly, the length L2 corresponding to the position of the prism 13 which is moved in the predetermined steps can be calculated The obtained axial length is stored in the memory 85, and is displayed on the monitor 81.

According to the above-described configuration, the axial length can be accurately measured since the light reflected from the cornea and the light reflected from the fundus are not made to interfere with each other. In addition, a burden on the eye can be reduced since the light which is projected onto the eye can be softened. Further, the axial length can be measured at a high S/N ratio by using spectral interference.

Incidentally, the present invention is not limited to the above-described technique, and the technique may be arranged such that the interference signals in the course of the movement of the prism 13 from the reference position in the arrow A direction are monitored, and the position of the prism 13 at the time when the interference signal AC and the interference signal PR have a predetermined positional relationship in the depth direction (e.g., there is a distance of L mm between the interference signal AC and the interference signal PR in the depth direction) is specified.

In addition, in the preferred embodiment, the grating mirror (diffraction grating) is used as the dispersing unit arranged to disperse synthesized light (interference light) generated by the measurement light and the reference light into the frequency components; however, a transmissive type grating, a prism, an acoustic optical element, or the like may be used as the dispersing unit.

Incidentally, the ocular depth dimension measurement apparatus in the preferred embodiment including a projecting optical system arranged to project measurement light onto the fundus Ef, and a photo-receiving optical system arranged to photo-receive the measurement light reflected from the fundus Ef may further include an eye refractive power measurement optical system arranged to measure eye refractive power of the eye E based on a signal from a photo detector of the photo-receiving optical system. Then, based on the eye refractive power obtained by the eye refractive power measurement optical system, the members placed inside the dotted lines in FIGS. 1A and 1B (the members placed at the light source 1 side with respect to the lens 8) are moved integrally in a direction of an arrow B (a direction of the optical axis La) by the visibility (diopter scale) correcting unit 800, whereby visibility of the eye is corrected. Accordingly, the light from the light source 1 is collected on the fundus Ef with efficiency, and the axial length can be accurately measured regardless of the eye refractive power of the eye E.

Figure 6:
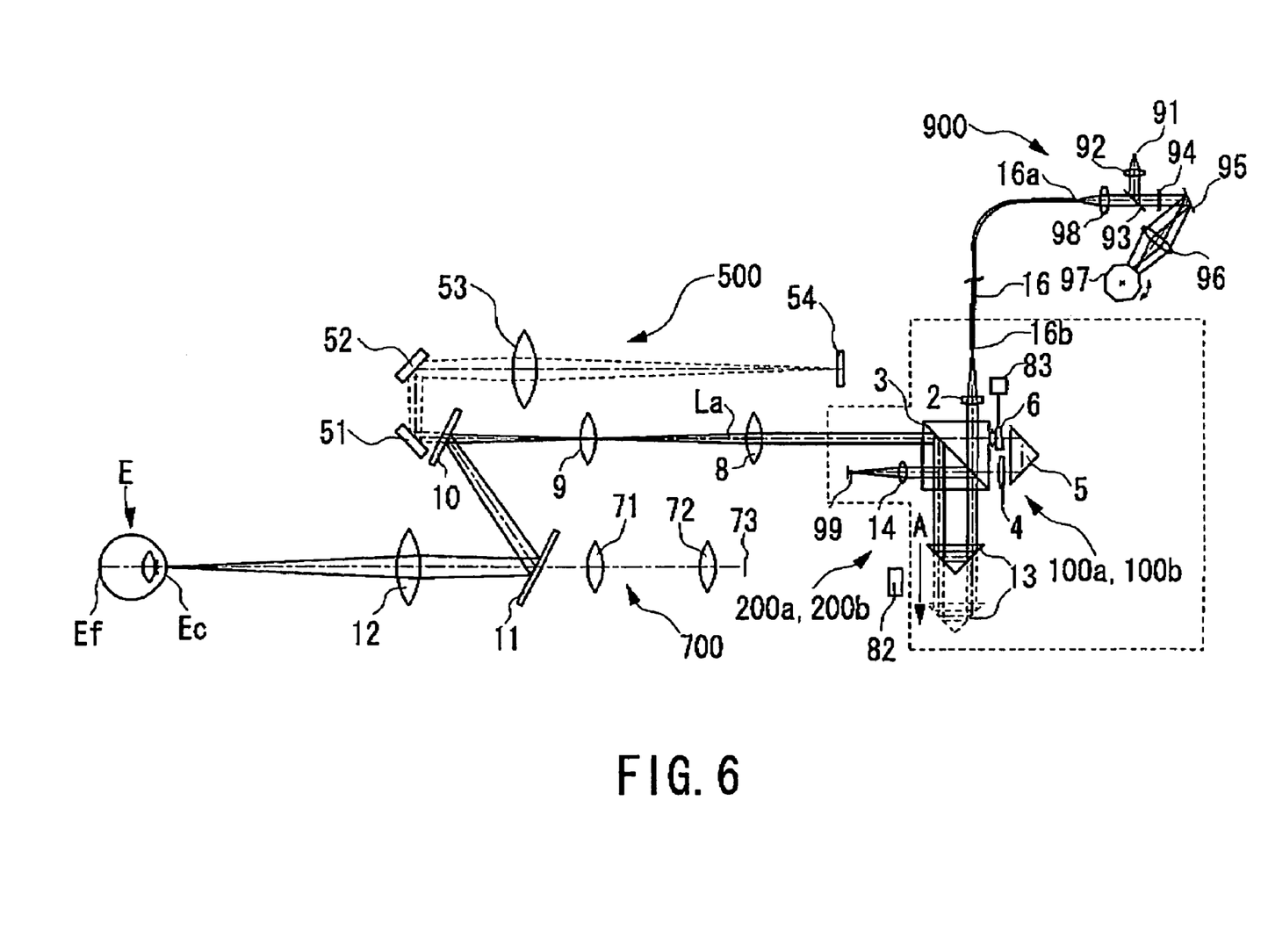
FIG. 6 is a view showing a schematic configuration of a modified embodiment of the optical system of the ocular depth dimension measurement apparatus.

In addition, in the preferred embodiment, the one-dimensional photodetector (line sensor) 64 is used as a photo-receiving unit of the spectrometer part; however, instead of using the photodectector 64, the ocular depth dimension measurement apparatus may be configured so that a wavelength changeable light source part 900 is used, and a single photodetector 99 such as a photodiode and an APD (avalanche photodiode) instead of an optical fiber 15 is used. The photodetector 99 has photo-receiving sensitivity to the infrared range much higher than the one-dimensional photodetector.

As shown in FIG. 6, the wavelength changeable light source part 900 includes a light source 91 such as an infrared SLD, a collimator lens 92, a polarization beam splitter 93, a ¼ wavelength plate 94, a grating mirror 95, a lens group 96, a polygon mirror 97, and a condenser lens 98. The polarization beam splitter 93 has properties of reflecting an S wave and transmitting a P wave.

The lens group 96 which includes a plurality of lenses is placed between the grating mirror 95 and the polygon mirror 97, and is designed so that principal rays of light in frequency components intersect at one point while the light in the frequency components which is reflected by the grating mirror 95 so as to be made into parallel light bundles and enters the lens group 96 is maintained so as to be parallel light bundles also after refraction. In addition, the polygon mirror 97 is placed so that a rotation axis thereof coincides with the point where the principal rays of the light in the frequency components intersect with each other.

Light from the light source 91 is made into a parallel light bundle by the lens 92, and only the light of the S wave is reflected by the polarization beam splitter 93, is transmitted through the ¼ wavelength plate 94, is dispersed into the frequency components by the grating mirror 95, is transmitted through the lens group 96, and is reflected by the polygon mirror 97. The polygon mirror 97 is rotated at a predetermined speed, and in accordance with the angle of its reflection surface, only the light in a specific frequency component travels in reverse on an optical path where the light has passed. The reverse light is transmitted through the lens group 96, is reflected by the grating mirror 95, is transmitted through the ¼ wavelength plate 94 so as to be made into the light of the P wave, is transmitted through the polarization beam splitter 93, and is collected on an end portion 16a of an optical fiber 16 in chronological order by the lens 98. Then, the light entering the end portion 16a exits from an end portion 16b of the optical fiber 16. Thus, when the polygon mirror 97 is continuously rotated, the light of which the frequency changes in chronological order is projected onto the eye E, and the light reflected from the eye E is photo-received on the photodetector 99. Accordingly, interference light in the respective frequency components can be continuously obtained as a function of time, based on which spectral information can be obtained. Then, the calculation and control part 80 controls to obtain eye characteristics of the eye E in the depth direction based on interference signals obtained by performing the Fourier analysis on the spectral information. Therefore, by using the single photodetector, the photo-receiving sensitivity can be enhanced and the axial length can be accurately measured.

Incidentally, in this configuration, the polygon mirror is used as a unit arranged to make the photodetector 99 photo-receive the light dispersed into the respective frequency components in chronological order; however, it is essential only that the unit is such as a galvano mirror which can make a photodetector photo-receive the light dispersed into the respective frequency components sequentially and time-divisionally. In addition, a wavelength changing unit including the grating mirror 95 and the polygon mirror 97 may be placed in front of the photodetector 99.

In addition, in this configuration, the light reflected by the polygon mirror 97 travels in reverse on the optical path, is transmitted through the polarization beam splitter 93 and is projected onto the eye E; however, it may be arranged that the light transmitted through the lens group 96 is reflected by the polygon mirror 97 in a different direction (a direction such that the light does not return to the lens group 96), is transmitted through the lens 98 and the optical fiber 16 placed in the reflecting direction, and is projected onto the eye E. In this case, it is essential only that the polygon mirror 97 is placed so that the rotation axis thereof does not coincide with the point where the principal rays of the light of the frequency components intersect with each other.

In addition, in this configuration, the SLD is used as the light source 91; however, it may be arranged that a wideband laser medium is used, and a wavelength scanning laser which turns back light of a selected wavelength to the laser medium is used.

In addition, in the preferred embodiment, the measurement light is collected on the cornea Ec; however, it is essential only that the measurement light reflected from the cornea Ec is dispersed into the frequency components and is photo-received on the photodetector; for example, it is essential only that the measurement light is collected in the vicinity of the cornea Ec, e.g., the pupil.

In addition, in the above description, the axial length is calculated based on the interference signals obtained by performing the Fourier analysis on the spectral information obtained by the photodetector 64 or the photodetector 99; however, the ocular depth dimension measurement apparatus may be configured so that a change in the spectral information obtained by the photodetector 61 or the photodetector 99 is taken as an interference signal, based on which the axial length is calculated.

In addition, in the above description, the prism 13 is moved simply in one direction during the axial length measurement; however; the prism 13 may be reciprocated on the order of a few times to Len-odd times per second, for example.

Incidentally, in this configuration, when the low coherent light is emitted from the light source 1 so as to measure the axial length, the prism 6 placed at the position deviated from the positions conjugate with the fundus Ef and the pupil is rotated, and thereby a convergent position of the fundus measurement light on the fundus Ef is moved in the direction perpendicular to the optical axis La. Accordingly, the interference signals detected at the photodetector 64 change in accordance with the change of the convergent position.

Figure 7:
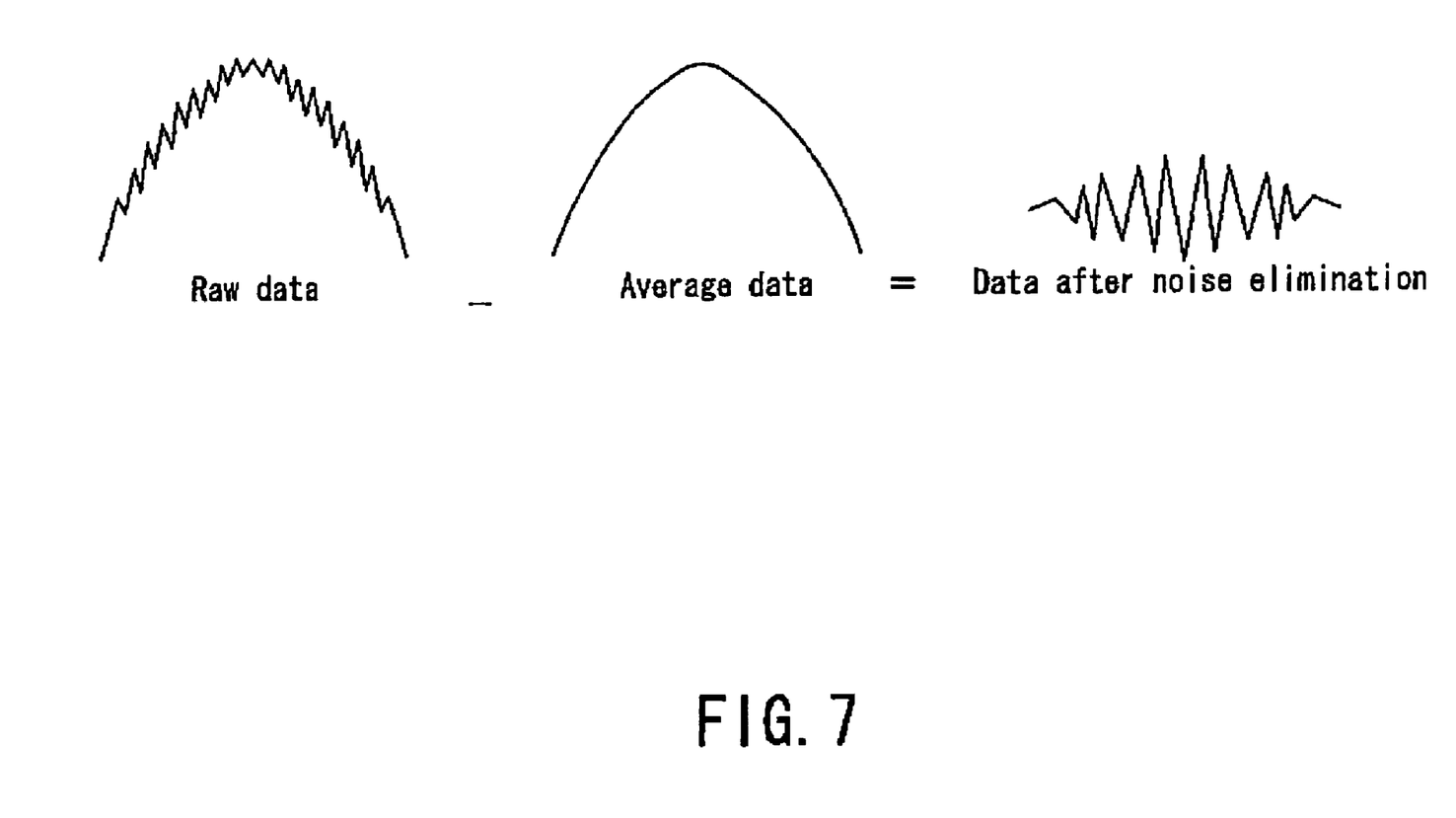
FIG. 7 is a view for illustrating a method of eliminating an FPN (Fixed Pattern Noise).

The calculation and control part 80 calculates the total sum of the spectral information obtained in plural times at the photodetector 64, and averages the spectral information. For example, luminance levels of respective pixels of the photodetector 64 are added by the pixel and the total sum of the spectral information is calculated, and the total sum is divided by the number of the spectral information obtainment so as to calculate average data on the spectral information. Besides, the average data on the spectral information is calculated for each movement position of the prism 13. The average data corresponds to an FPN (Fixed Pattern Noise) existing fixedly in the interference signals regardless of the convergent position of the fundus measurement light. Accordingly, the calculation and control part 80 subtracts the average data corresponding to the FPN from raw data on the spectral information which is obtained at the photodetector 64 in chronological order, thereby obtaining the spectral information from which the FPN is eliminated (see FIG. 7), and calculating the axial length based on the interference signals obtained based on the spectral information from which the FPN is eliminated. Therefore, a measurement error due to the FPN can be avoided.

Incidentally, in this configuration, the FPN which is produced in the interference light generated by the fundus measurement light and the reference light is eliminated; however, the ocular depth dimension measurement apparatus may be configured so that the FPN produced in the interference light generated by the corneal measurement light and the reference light is eliminated. That is to say, a light deflection member (e.g., the prism 6) which deflects the corneal measurement light may be placed at a position deviated from a position conjugate with the cornea Ec on the optical path of the projecting optical system 200a. In addition, by placing the light deflection member at a position deviated from positions conjugate with the fundus Ef and conjugate with the cornea Ec on the common optical path of the projecting optical systems 100a and 200a, the FPNs which are produced in the respective interference light can be eliminated.

In addition, by placing the light deflection member at a position deviated from a position conjugate with the pupil on the common optical path of the projecting optical system 100a and the photo-receiving optical system 100b, the fundus measurement light projected onto the fundus Ef and the fundus measurement light reflected from the fundus Ef pass through different positions in the vicinity of the pupil. Accordingly, even if the eye E has an obstacle such as cataract, the axial length can be measured while an influence of noise light due to the cataract or the like is reduced.

Incidentally, in the case of eliminating the FPN, it is essential only that the convergent (projection) position of the measurement light is moved in the direction perpendicular to the optical axis La. For example, the light source 1 may be moved in the direction perpendicular to the optical axis La.

Incidentally, in the preferred embodiment, a configuration such that the ocular depth dimension of the examinee's eye (the axial length, a depth dimension of the anterior segment, and the like) can be obtained is described; however, the ocular depth dimension measurement apparatus maybe configured so that a scanning unit (e.g., a galvano mirror) arranged to scan the measurement light projected onto the examinee's eye in a predetermined direction is provided so as to obtain a tomographic image of the examinee's eye. For example, by providing the scanning unit arranged to scan the measurement light collected on the fundus Ef in a predetermined direction perpendicular to the optical axis La, the tomographic image of the fundus Ef can be obtained. To be specific, the scanning unit is placed at a position approximately conjugate with the pupil between the half mirror 10 and the eye E.

In addition, by providing the scanning unit arranged to scan the measurement light collected in the vicinity of the cornea Esc in the predetermined direction perpendicular to the optical axis La, a tomographic image of the anterior segment can be obtained. To be specific, the scanning unit is placed at a focal position of the lens 12.

Incidentally, in the case of obtaining the tomographic image by the apparatus in the preferred embodiment, it is preferable, in order to prevent interference light which is generated by synthesizing light reflected by a measurement surface on which the tomographic image is not obtained and the reference light from being photo-received on the photodetector 64, to provide a shielding member which prevents the interference light which is generated by synthesizing the measurement light projected onto the measurement surface on which the tomographic image is not obtained and the reference light from being photo-received thereon. For example, it is essential only that the half mirror 3 is replaced with a polarization beam splitter, a $\lambda/4$ plate is placed between the half mirror 10 and the reference mirror 54, and a polarization direction of the λ/4 plate is adjusted.

In addition, if the ocular depth dimension measurement apparatus is configured so that the measurement light is scanned in a two-dimensional direction perpendicular to the optical axis La, it is possible to obtain a three-dimensional fundus image, a three-dimensional anterior-segment image, and the like.

In addition, in the preferred embodiment, a configuration such that the reference light optical system for corneal measurement and the reference light optical system for fundus measurement are shared is described; however, the ocular depth dimension measurement apparatus may be configured so that the reference light optical systems are separated. Even in this configuration, the optical path length of the corneal measurement light and the optical path length of the reference light are maintained in a state of approximately coinciding constantly. Then, when the optical path length of the reference light is changed, the reference mirror (reference surface) may be moved, or the optical path of the reference light may be switched with time. When obtaining the optical path length of the reference light in order to measure the axial length, a positional signal of the reference mirror or a switching signal of the optical path of the reference light is used as the driving result of the optical path length changing unit.

In addition, in the preferred embodiment, a configuration such that the reference light is reflected by the reference mirror 54 and is synthesized with the corneal measurement light and the fundus measurement light is described; however, the ocular depth dimension measurement apparatus may be configured so that the reference light travels on an optical path formed by an optical fiber or the like and is synthesized with the corneal measurement light and the fundus measurement light without using the reference mirror 54.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ocular depth dimension measurement apparatus which performs non-contact measurement of an ocular depth dimension of an examinee's eye, the apparatus comprising:
    a measurement light projecting optical system including a light source emitting low coherent light, and arranged to make a part of the light from the light source into first measurement light and a part of the light from the light source into second measurement light, and to collect the first measurement light on a first measurement surface of the eye and the second measurement light on a second measurement surface of the eye;
    an interference optical system including:
        a separation unit arranged to separate a part of the light from the light source to make it into reference light; and
        an optical path length changing unit arranged to change optical path length of the reference light, arranged, while changing the optical path length of the reference light, to synthesize the first measurement light reflected by the first measurement surface and the reference light and to make them interfere with each other so as to photo-receive, and to synthesize the second measurement light reflected by the second measurement surface and the reference light and to make them interfere with each other so as to photo-receive, and arranged to obtain interference signals of respective interference light; and
    a calculation part arranged to calculate the ocular depth dimension of the eye based on the obtained interference signals and a driving result of the optical path length changing unit.

2. The ocular depth dimension measurement apparatus according to claim 1, wherein the optical path length changing unit is placed at a position which is on a common optical path of the first measurement light and the reference light and not on an optical path of the second measurement light, and is arranged to simultaneously change optical path length of the first measurement light and the optical path length of the reference light.

3. The ocular depth dimension measurement apparatus according to claim 1, wherein
    the interference optical system further includes a reference surface which reflects the reference light, the reference surface being placed so that the optical path length of the first measurement light and the optical path length of the reference light approximately coincide, and
    the optical path length changing unit changes the optical path length of the reference light while maintaining a state where the optical path length of the first measurement light and the optical path length of the reference light approximately coincide.

4. The ocular depth dimension measurement apparatus according to claim 3, wherein
    the interference optical system further includes:
        a first reference surface which reflects the reference light which is synthesized with the first measurement light, the first reference surface being placed to be fixed so that the optical path length of the first measurement light and the optical path length of the reference light which is synthesized with the first measurement light approximately coincide; and
        a second reference surface which reflects the reference light which is synthesized with the second measurement light, the second reference surface being placed to be movable, and
    the optical path length changing unit changes the optical path length of the reference light which is synthesized with the second measurement light by moving the second reference surface.

5. The ocular depth dimension measurement apparatus according to claim 1, wherein
    the interference optical system further includes a dispersing unit arranged to disperse the respective interference light into frequency components, and
    the calculation part calculates the ocular depth dimension based on interference signals which are obtained by performing Fourier analysis on interference signals of the frequency components and the driving result of the optical path length changing unit.

6. The ocular depth dimension measurement apparatus according to claim 1, wherein the interference optical system further includes a wavelength changing unit arranged to change a wavelength of the light from the light source, and the calculation part calculates the ocular depth dimension based on interference signals which are obtained by performing Fourier analysis on interference signals of wavelength components and the driving result of the optical path length changing unit.

7. The ocular depth dimension measurement apparatus according to claim 1, wherein the measurement light projecting optical system further includes a scanning unit arranged to scan the first measurement light on the first measurement surface or to scan the second measurement light on the second measurement surface, and the calculation part obtains a tomographic image of the eye based on an interference signal which is obtained by scanning the first measurement light or the second measurement light.

* * * * *